(12) United States Patent
Drew (10) Patent No.: US 7,510,447 B2
(45) Date of Patent: Mar. 31, 2009

(54) CONNECTOR AND CONTACT ASSEMBLIES FOR MEDICAL DEVICES

(75) Inventor: Michael H. Z. Drew, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 53 days.

(21) Appl. No.: 11/697,386

(22) Filed: Apr. 6, 2007

(65) Prior Publication Data
US 2008/0248690 A1 Oct. 9, 2008

(51) Int. Cl.
*H01R 24/04* (2006.01)
(52) U.S. Cl. ......................................... 439/669; 607/37
(58) Field of Classification Search ................. 439/668, 439/669, 909; 607/37, 38
See application file for complete search history.

(56) References Cited

U.S. PATENT DOCUMENTS

| | | | |
|---|---|---|---|
| 4,445,511 A | 5/1984 | Cowdery et al. | |
| 4,715,380 A | 12/1987 | Harris | |
| 5,275,620 A | 1/1994 | Darby et al. | |
| 5,769,671 A * | 6/1998 | Lim | 439/843 |
| 6,725,096 B2 | 4/2004 | Chinn et al. | |
| 6,741,892 B1 * | 5/2004 | Meadows et al. | 607/116 |
| 6,895,276 B2 * | 5/2005 | Kast et al. | 607/37 |
| 7,130,699 B2 | 10/2006 | Huff et al. | |
| 7,402,083 B2 * | 7/2008 | Kast et al. | 439/660 |
| 2005/0027325 A1 | 2/2005 | Lahti et al. | |
| 2005/0027326 A1 * | 2/2005 | Ries et al. | 607/37 |
| 2005/0027327 A1 | 2/2005 | Ries et al. | |

* cited by examiner

*Primary Examiner*—Neil Abrams
(74) *Attorney, Agent, or Firm*—Fredrickson & Byron, P.A.

(57) ABSTRACT

A contact assembly of a medical device includes a sidewall, surrounding a bore that receives axial insertion of a medical electrical lead connector; the bore extends along a longitudinal axis of the contact assembly, and first and second contact clips are mounted on, or attached to the sidewall, such that opposing first and second legs of each clip extend into the bore of the contact assembly. The mounted contact clips may be approximately 90 degrees offset from one another about a perimeter of the bore. The mounted contact clips may form a single electrical coupling, for example, if the sidewall is conductive, or individual and separate electrical couplings, for example, if the sidewall is non-conductive. The first and second legs of each contact clip may bend into and out from the bore, such that first and second terminal ends of each clip are located outside the bore.

46 Claims, 7 Drawing Sheets

CONNECTOR AND CONTACT ASSEMBLIES FOR MEDICAL DEVICES

TECHNICAL FIELD

The present invention pertains to medical device and more particularly to medical device connector assemblies and contact assemblies thereof.

BACKGROUND

A host of medical devices include electrical connector assemblies for coupling with a type of medical electrical lead connector that is formed along a proximal portion of the lead and includes a plurality of connector elements disposed along a length thereof. These connector assemblies typically include a plurality of electrical contacts positioned within a bore of what is typically called a device connector module, or header, at locations corresponding to the connector elements of the lead connector, in order to mate with the corresponding connector elements when the connector is fully inserted within the bore. Some device connector assemblies further include sealing elements located between the electrical contacts to mate with insulative spacers located between the connector elements of the lead connector, and thereby provide electrical isolation between each mating contact and connector element. Although a variety of contact assemblies for such connector assemblies are known in the art, there is still a need for new contact assembly designs that provide for stable electrical connection without increasing a bulk, complexity or cost of the connector assemblies.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1A:
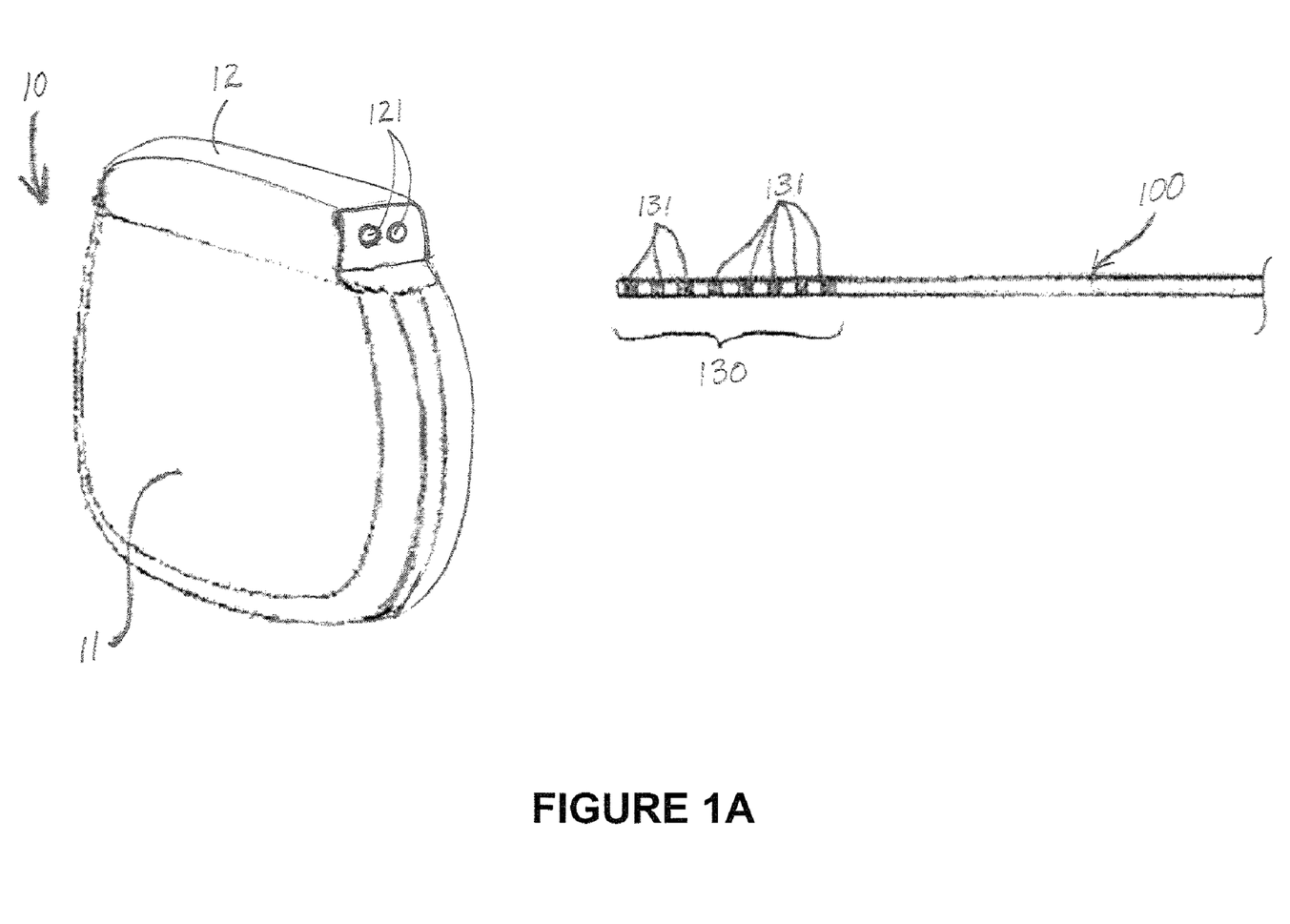
FIG. 1A is perspective view of a portion of an exemplary medical system that may include embodiments of the present invention.

FIG. 1A is perspective view of a portion of an exemplary medical system that may include embodiments of the present invention. FIG. 1A illustrates the medical system including a medical device 10 and a medical electrical lead 100; a connector 130 of lead 100 is shown terminating a proximal end thereof and including a plurality of connector elements 131 spaced apart along a length of connector 130 by a plurality of interposed insulative spacers. Materials, components and construction methods for lead connectors, such as connector 130, are well known to those skilled in the art. FIG. 1A further illustrates device 10 including a housing 11 and a connector module 12 mounted thereto; module 12 includes a pair of bores 121 formed by connector assemblies 120, which are contained within module 12 and are shown in FIG. 1B.

Figure 1B:
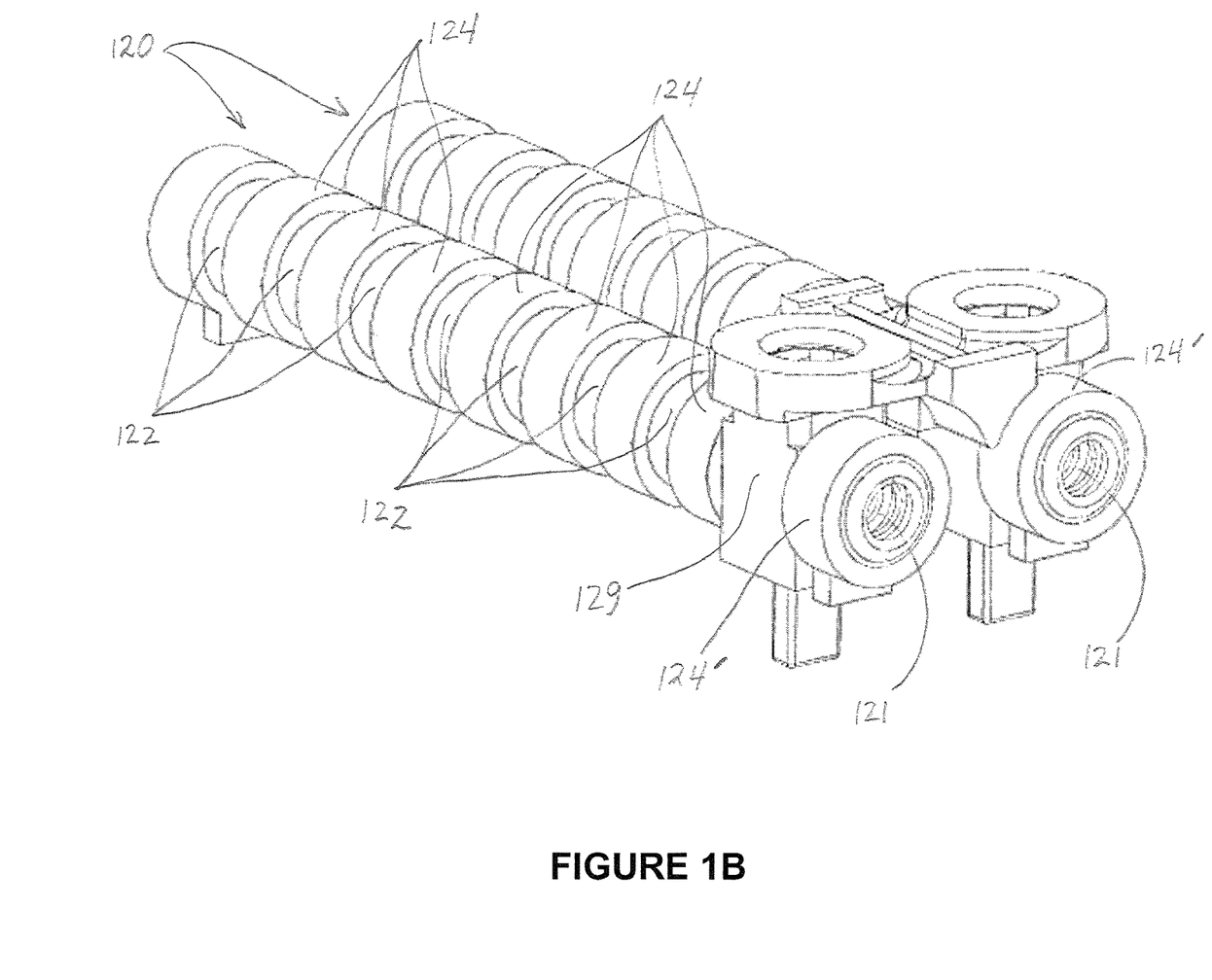
FIG. 1B is a perspective view of a pair of connector assemblies from the system show in FIG. 1A, according to an exemplary embodiment of the present invention.

FIG. 1B is a perspective view of connector assemblies 120, according to an exemplary embodiment of the present invention. FIG. 1B illustrates each connector assembly 120 including a plurality of contact assemblies 122, 129 spaced apart from one another, by a plurality of seal members 124, along a length of bore 121. According to the illustrated embodiment, contact assembly 129 is a set screw-type contact known to those skilled in the art. A location of each contact assembly 122, 129 corresponds to a location of each connector element 131 of lead connector 130 to provide electrical coupling between the corresponding connector element 131 and circuitry contained within housing 11, when connector 130 is fully inserted into either of bores 121; and interspersed seal members 124 provide electrical isolation between the couplings. An additional sealing member 124' is shown located at an entry to each bore; sealing members 124' may prevent an ingress of bodily fluids into bore 121, for example, if device 10 is an implantable device. Those skilled in the art will appreciate that module 12, for example, formed from either silicone or polyurethane, or a combination thereof, may be molded around connector assemblies 120 and includes passages or wire-ways for routing of lead wires from contact assemblies 122 to corresponding feedthrough ports which extend through housing 11; if device 10 is implantable, the feedthrough ports are hermetically sealed. Connector assemblies 120, as a whole, will be discussed in greater detail, below, in conjunction with FIG. 7.

Figure 2:
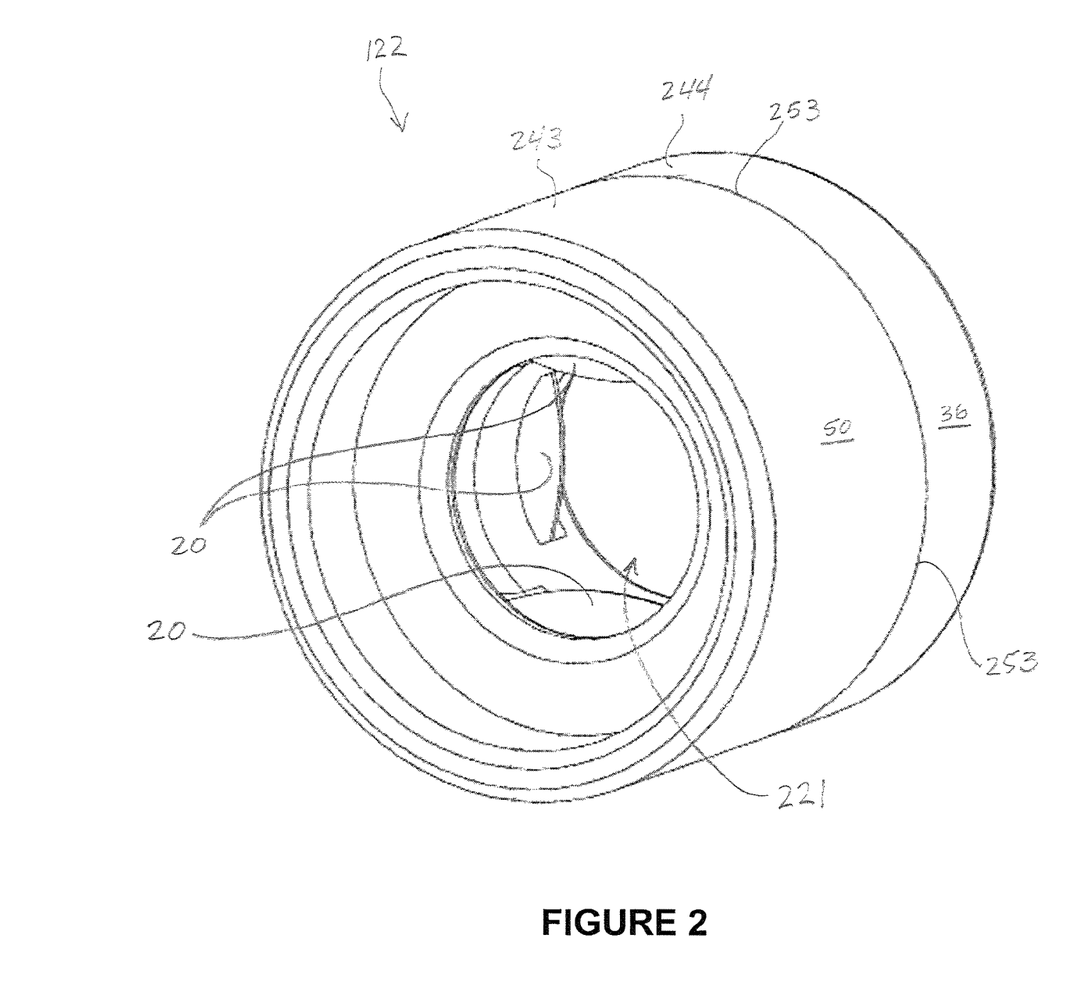
FIG. 2 is a perspective view of a contact assembly, according to some embodiments of the present invention.

FIG. 2 is a perspective view of one of contact assemblies 122, according to some embodiments of the present invention. FIG. 2 illustrates contact assembly 122 including a bore 221, which forms a portion of bore 121 (FIGS. 1A-B), and contact surfaces 20 protruding into bore 221. According to some embodiments, when lead connector 130 is inserted within one of bores 121 formed by connector assemblies 120, such that one of lead connector elements 131 is aligned with contact surfaces 20 within bore 221, surfaces 20 make electrical contact with the aligned connector element 131. FIG. 2 further illustrates contact assembly 122 including two members 243, 244, embodiments of which are described in greater detail in conjunction with FIGS. 3-5; the members are called a cup member 243 and a mounting member 244 in the following description.

Figure 3:
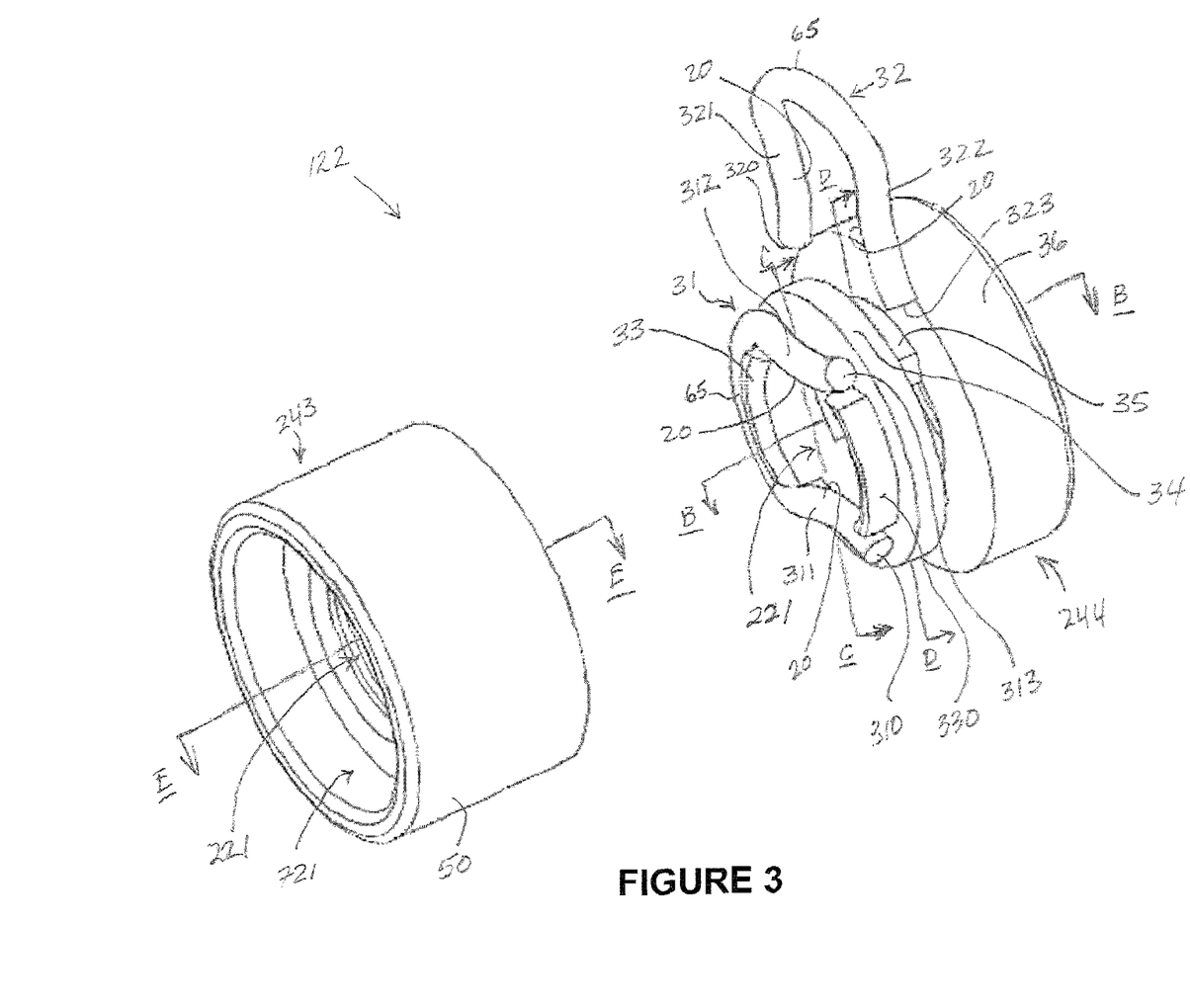
FIG. 3 is an exploded perspective view of the contact assembly of FIG. 2, according to some embodiments of the present invention.
Figure 4A:
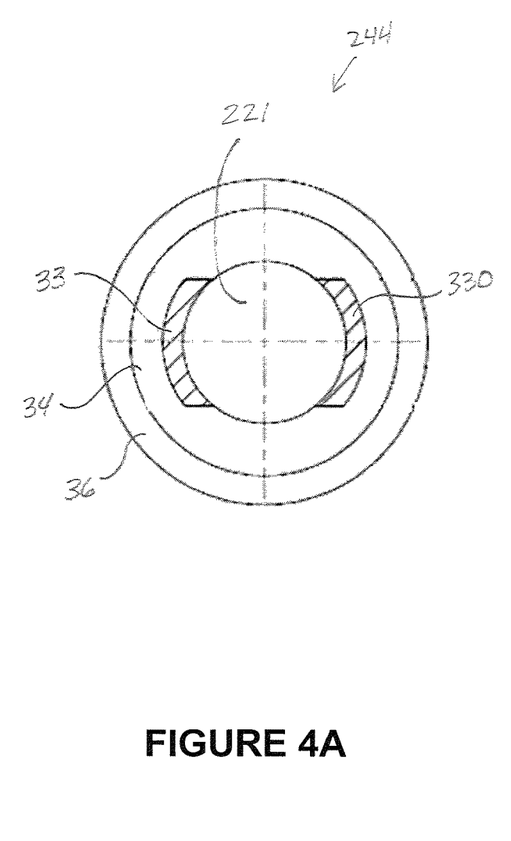
FIGS. 4A-C are cross-sections of a component of the contact assembly shown in FIG. 3, along FIG. 3 section lines C-C, D-D, and B-B, respectively.
Figure 4B:
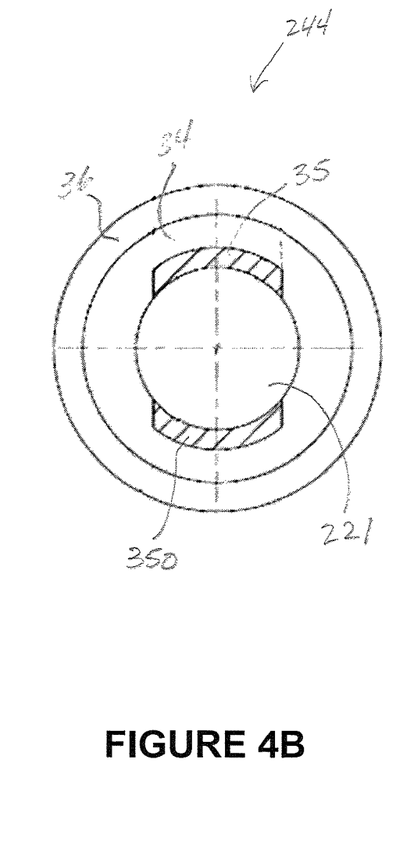
Figure 4C:
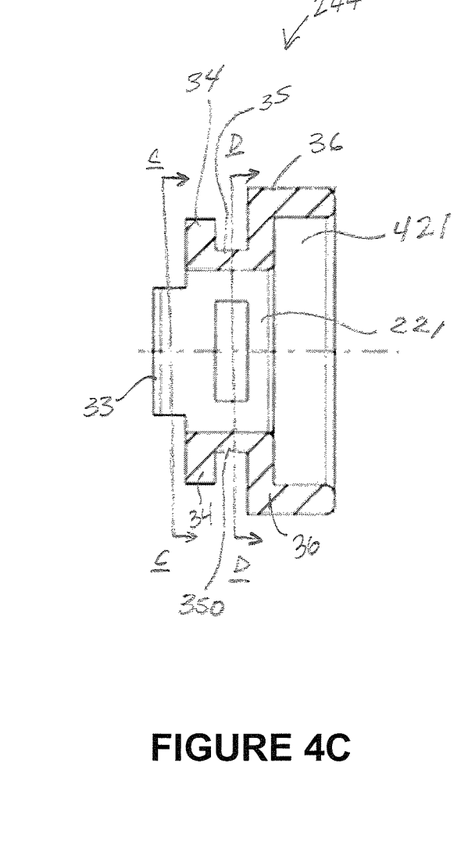

FIG. 3 is an exploded perspective view of contact assembly 122, according to some embodiments of the present invention. FIG. 3 illustrates contact surfaces 20 located along first and second legs 311, 312 of a first contact clip 31 and along first and second legs 321, 322 of a second contact clip 32. According to the illustrated embodiment, a sidewall of mounting member 244, that extends about bore 221, includes first and second mounting sidewalls 33, 35, which each provide for the mounting, or attachment of a corresponding contact clip 31, 32, such that contact surfaces 20 thereof protrude into bore 221. With further reference to FIG. 3, it may be appreciated that each of mounting sidewalls 33, 35 only extend about a portion of a perimeter of bore 221 to allow for legs 311, 312 and 321, 322 to extend into bore 221, and that sidewalls 33, 35 are axially offset from one another, that is, offset from one another along a longitudinal axis of member 244. With reference to FIGS. 4A-B, which are cross-section views of component 244, without clips 31, 32, through lines C-C and D-D of FIG. 3, it may further be appreciated that the portions of the perimeter of bore 221 about which sidewalls 33, 35 extend are offset, about the perimeter, from one another by approximately ninety degrees. It should be noted that although bore 221 has a round cross-section, so that the perimeter thereof defines a circumference of the bore, embodiments of the present invention are not limited to including bores having round cross-sections.

With further reference to FIG. 3, the sidewall of mounting member 244 includes a shoulder 34 located between first and second mounting sidewalls 33, 35; shoulder 34 may stabilize the mounting of first and second contact clips 31, 32 with respect to one another, when clips 31, 32 are attached to mounting sidewalls 33, 35, respectively. Although FIG. 3 illustrates a preferred embodiment in which shoulder 34 extends about an entirety of the perimeter of bore 221, it should be noted that an extent of shoulder 34 can be more limited, according to alternate embodiments, for example, as shown by the shading bounded by dashed lines in FIGS. 4A-B. FIG. 3 further illustrates another shoulder 36 axially offset from shoulder 34 and located alongside second mounting sidewall 35. According to the illustrated embodiment, shoulder 36 extends about the entirety of the perimeter of bore 221 and, with reference to FIG. 4C, which is a cross-section view through section line B-B of FIG. 3, shoulder 36 extends axially away from second mounting sidewall 35 to surround a counter-bore 421 of mounting member 244. Like shoulder 34, as previously described, shoulder 36, according to alternate embodiments, can extend about only a portion of the perimeter of bore 221. Shoulder 36 may serve to further stabilize the mounting of second clip 32, and the extent of shoulder 36 which surrounds counter-bore 421 can interlock with an adjacent member of connector assembly 120, as will be described below in conjunction with FIG. 7.

FIGS. 3 and 4A-C further illustrate a first opposing sidewall 330, opposite first mounting sidewall 33, and a second opposing sidewall 350, opposite second mounting sidewall 35. With particular reference to FIGS. 4A-B, it may be appreciated that first and second opposing sidewalls 330, 350 extend about portions of the perimeter of bore 221 which are offset from the corresponding mounting sidewalls 33, 35 by approximately 180 degrees. According to the illustrated embodiment, first and second opposing sidewalls 330, 350 and first and second mounting sidewalls 33, 35, respectively, are symmetric; such symmetry may be advantageous for ease, or flexibility of assembly, since opposing sidewalls 330, 350 can serve as alternative mounting sidewalls for contact clips 31, 32. According to some embodiments, first and second opposing sidewalls 330, 350 interface with contact clip legs 311, 312 and 321, 322, in proximity to contact clip terminal ends 310, 313 and 320, 323, respectively, in order to pre-load clips 31, 32, respectively. Pre-loading will be described in greater detail, below, in conjunction with FIG. 6.

Figure 5:
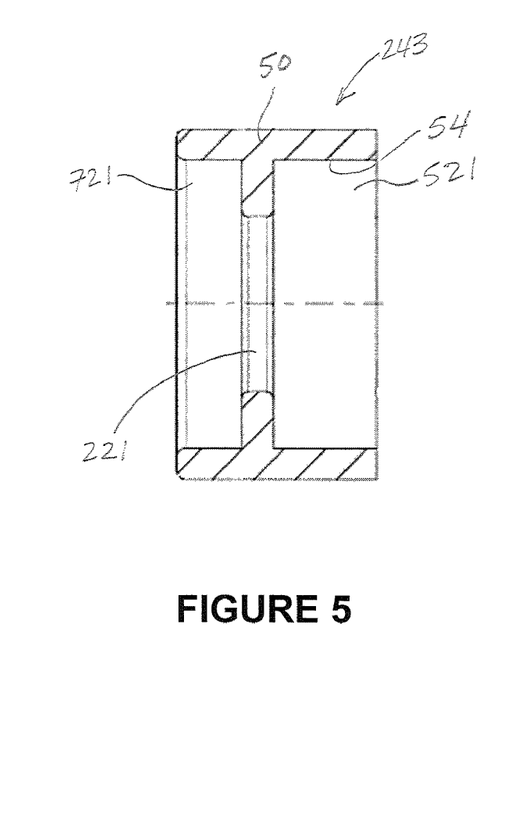
FIG. 5 is a cross-section of another component of the contact assembly shown in FIGS. 2 and 3, along section line E-E of FIG. 3.
Figure 7:
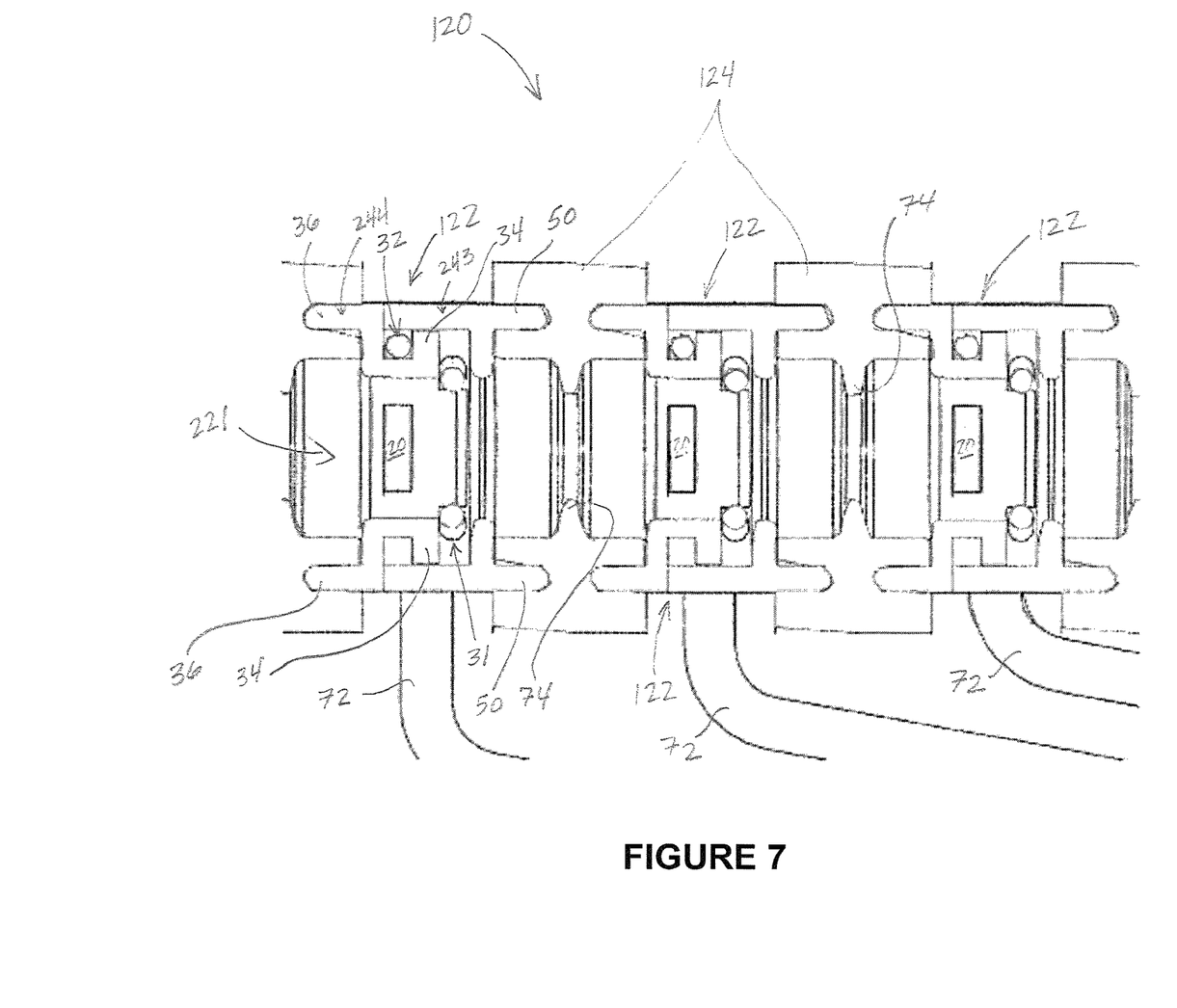
FIG. 7 is a longitudinal cross-section along a portion of the one of the connector assemblies shown in FIG. 1B, according to some embodiments of the present invention.

FIG. 5 is a cross-section view through cup member 243 of contact assembly 122, along section line E-E shown in FIG. 3. FIGS. 3 and 5 illustrate cup member 243 including a sidewall 50 surrounding bore 221 and two counter-bores 521, 721 extending on either side of bore 221. According to the illustrated embodiment, when cup member 243 is assembled together with mounting member 244, that has clips 31, 32 attached thereto, for example, as shown in FIGS. 2 and 7, clips 31, 32 are contained in counter-bore 521, and an inner surface 54 of sidewall 50 surrounding counter-bore 521 fits snugly about shoulder 34 of mounting member 244. The extent of sidewall 50 that surrounds counter-bore 721 can interlock with an adjacent member of connector assembly 120, as will be described below in conjunction with FIG. 7.

Figure 6:
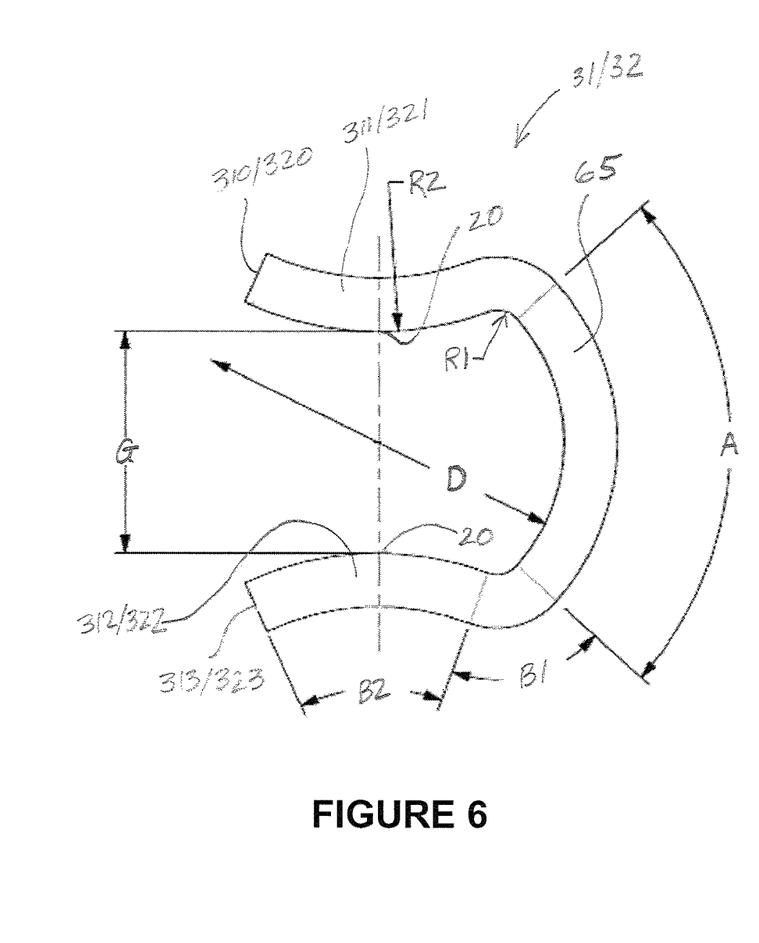
FIG. 6 is a plan view of a contact clip, according to some embodiments of the present invention.

FIG. 6 is a plan view of either of clips 31, 32. FIG. 6 illustrates clip 31/32 including a joining portion 65; joining portion 65 is shown extending between first and second legs 311/321, 312/322, being curved about a circumference of a circle having a diameter D, and spanning a segment of the circle that has a central angle A. FIG. 6 further illustrates each leg 311/321, 312/322 bending inward, toward one another, and then outward away from one another; the inward bending, or curvature, of each leg 311/321, 312/322 extends about a circumference of a circle having a radius R1, and spans a segment of the circle that has a central angle B1, and the outward bending, or curvature, of each extends about a circumference of a circle having a radius R2, and spans a segment of the circle that has a central angle B2. With reference back to FIG. 3, it may be appreciated that joining portion 65 of each clip 31, 32 rests on, and approximately spans the corresponding mounting sidewall 33, 34, that the inward bending of legs 311/321, 312/322 results in the protrusion of contact surfaces 20 into bore 221, and that the outward bending of legs 311/321, 312/322 keeps terminal ends 310/320, 313/323 located outside bore 221, as well as facilitating a rather easy assembly of clips 31/32 onto the sidewall of mounting member 244. According to preferred embodiments of the present invention, clip 31/32 is formed from a wire having a round cross-section, although any cross-sectional geometry may be employed by alternate embodiments.

FIG. 6 further illustrates a relaxed gap G between a peak of the outward bending of leg 311/321 and a peak of the outward bending of leg 312/322. According to the illustrated embodiment, these peaks form opposing contact surfaces 20 and gap G is opened up by insertion of a lead connector, for example, connector 130 (FIG. 1A) therebetween; a spring force of clips 31/32 applies an appropriate contact pressure of contact surfaces 20 against the corresponding connector element 131 positioned within bore 221 of the corresponding contact assembly 122. As mentioned above, opposing sidewalls 330, 350, opposite mounting sidewalls 33, 35, according to some embodiments of the present invention, provide an interface for pre-loading of clips 31, 32. Sidewall 330/350 can pre-load clip 31/32 by spreading opposing legs 311/321, 312/322 further apart from one another and holding a gap between therebetween which is wider than relaxed gap G. Such pre-loading may decrease an axial force required to insert a connector into a connector assembly that includes contact assemblies 122, for example, connector 130 into connector assembly 120.

According to an exemplary embodiment of the present invention, for connector elements, for example, elements 131 of connector 130 (FIG. 1A), which have an outer diameter between approximately 0.044 inch and approximately 0.052 inch, and in which clips 31/32 are not pre-loaded: relaxed gap G is between approximately 0.041 inch and approximately 0.043 inch; diameter D of the circle defining joining portion 65 is between approximately 0.069 inch and approximately 0.071 inch, and central angle A of the segment of the circle defining joining portion 65 is between approximately 82 degrees and approximately 85 degrees; radius R1 of the circle defining the inward bending of legs 311/321, 312/322 is between approximately 0.004 inch and approximately 0.006 inch, and the central angle B1 of the segment of the circle defining the inward bending is between approximately 67 degrees and approximately 70 degrees; and radius R2 of the circle defining the outward bending of legs 311/321, 312/322 is between approximately 0.059 inch and approximately 0.061 inch, and the central angle B2 of the segment of the circle defining the outward bending is between approximately 44 degrees and approximately 46 degrees. An outer diameter of mounting sidewall 33/35, and optionally opposing sidewall 330/350, is between approximately 0.069 inch and approximately 0.071 inch for a line-to-ling fit of clip 31/32 thereon, according to the exemplary embodiment; and an inner diameter of sidewall 33/35 and 330/350 may be approximately 0.056 inch for the exemplary embodiment. Those skilled in the art will understand that these exemplary dimensions may be modified according to various diameters of connector elements 131 and/or if pre-loading is desired.

FIG. 7 is a longitudinal cross-section along a portion of connector assembly 120 (FIG. 1B), according to some embodiments of the present invention. FIG. 7 illustrates a lead wire 72 coupled to each of contact assemblies 122; as previously described, a module, for example, module 12 (FIG. 1A), which contains connector assembly 120, may include wire-ways providing for the routing of each of lead wires 72 to the corresponding feedthrough port. According to an exemplary embodiment of the present invention, each of clips 31, 32, mounting member 244 and cup member 243 are formed from MP35N alloy; alternative conductive materials from which these components may be formed include, without limitation, stainless steel, titanium, tantalum and platinum-iridium. Thus, according to the illustrated embodiment, a fit of cup member 243 over mounting member 244 and clips 31, 32, being mounted thereon, provides intimate contact therebetween for electrical coupling so that lead wires 72, being coupled to cup member 243, power clips 31, 32; alternately, lead wires 72 may be coupled to mounting member 244. With reference back to FIG. 2, in conjunction with FIG. 7, it will be appreciated that an outer diameter of cup member sidewall 50 is approximately equal to an outer diameter of mounting member shoulder 36; as previously described, an inner surface 54 of cup member sidewall 50 (FIG. 5) fits snugly about mounting member shoulder 34, and an interface, or seam 253 between sidewall 50 and shoulder 36 may be laser or resistance spot welded to secure members 243, 244 together.

According to some alternate embodiments, one or both of members 243, 244 are formed from a non-conductive material, for example, a hard plastic or ceramic. If one of members 243, 244 is non-conductive, lead wires 72 may be coupled to the other of members 243, 244, or directly to contact clips 31, 32, in order to power clips 31, 32. If neither of members 243, 244 is conductive, lead wires 72 may be coupled directly to each of clips 31, 32, for example, via a wire-way formed through one of members 243, 244.

FIG. 7 further illustrates seal members 124 including internally-projecting sealing rings 74, for mating with insulative spacers disposed between connector elements 131 of connector 130 (FIG. 1A), and an interlocking of each seal member 124 with adjacent contact assemblies 120. As previously described, mounting member shoulder 36 extends to provide for the interlocking, as does cup member sidewall 50. The illustrated interlocking features of connector assembly 120 are described in greater detail in commonly-assigned U.S. Pat. No. 6,895,276, salient portions of which are hereby incorporated by reference.

In the foregoing detailed description, the invention has been described with reference to specific embodiments. However, it may be appreciated that various modifications and changes can be made without departing from the scope of the invention as set forth in the appended claims. For example, although embodiments of a contact assembly presented herein include a pair of contact clips, for example, clips 31, 32, to make common electrical contact with a single lead connector element, for example, one of elements 131, each clip of the pair of contact clips may be isolated from one another within the contact assembly, for example, via mounting member 244 being formed from a non-conductive material, and individually coupled to independent lead wires for electrical coupling of two independent lead connector elements having been inserted within the contact assembly.

I claim:

1. A contact assembly for a connector module of a medical device, the contact assembly comprising:

a mounting member including a bore extending along a longitudinal axis of the assembly, a first mounting sidewall extending about a first portion of a perimeter of the bore, a second mounting sidewall being axially offset from the first mounting sidewall and extending about a second portion of the perimeter of the bore, the second portion being offset about the perimeter from the first portion by approximately ninety degrees, and a shoulder extending about the first and second portions of the perimeter of the bore and being axially located between the first and second mounting sidewalls;

a first contact clip mounted on the first mounting sidewall, the first contact clip including a first terminal end and a first leg extending into the bore and being terminated at the first terminal end on an opposite side of the bore from the first mounting sidewall, and a second terminal end and a second leg extending into the bore on an opposite side of the bore from the first leg, and being terminated at the second terminal end on the opposite side of the bore from the first mounting sidewall; and a second contact clip mounted on the second mounting sidewall, the second contact clip including a first terminal end and a first leg extending into the bore and being terminated at the first terminal end of the second clip on an opposite side of the bore from the second mounting sidewall, and a second terminal end and a second leg extending into the bore on an opposite side of the bore from the first leg of the second contact clip, and being terminated at the second terminal end of the second clip on the opposite side of the bore from the second mounting sidewall;

wherein the bore receives an axial insertion of a medical electrical lead connector therein.

2. The contact assembly of claim 1, wherein the mounting member further includes a first opposing sidewall, opposite the first mounting sidewall, being approximately axially aligned with the first mounting sidewall, the first opposing sidewall extending about a third portion of the perimeter of the bore, the third portion being offset from the first portion by approximately 180 degrees, and a second opposing sidewall, opposite the second mounting sidewall, being approximately axially aligned with the second mounting sidewall, the second opposing sidewall extending about a fourth portion of the perimeter of the bore, the fourth portion being offset from the second portion by approximately 180 degrees.

3. The contact assembly of claim 2, wherein the first mounting sidewall and the first opposing sidewall are symmetric.

4. The contact assembly of claim 2, wherein the first opposing sidewall interfaces with the first and second legs of the first contact clip in proximity the first and second terminal ends, respectively, of the first clip in order to pre-load the first clip.

5. The contact assembly of claim 1, wherein the shoulder of the mounting member extends about an entirety of the perimeter of the bore.

6. The contact assembly of claim 1, wherein the first and second legs of the first contact clip bend into and out from the bore such that the first and second terminal ends of the first clip are located outside the bore.

7. The contact assembly of claim 1, wherein the first contact clip is formed from a wire having a round cross-section.

8. The contact assembly of claim 1, wherein the mounting member further comprises another shoulder being axially offset from the shoulder that extends about the first and second portions of the perimeter of the bore, the other shoulder extending around the second portion of the perimeter of the bore and being located alongside the second mounting sidewall.

9. The contact assembly of claim 8, wherein the other shoulder of the mounting member extends about an entirety of the perimeter of the bore.

10. The contact assembly of claim 9, wherein:
the mounting member further includes a counter-bore extending from the bore, along the longitudinal axis, the counter-bore having a diameter larger than that of the bore; and
the other shoulder extends axially away from the second mounting sidewall to surround the counter-bore.

11. The contact assembly of claim 1, further comprising:
a cup member, the cup member including a sidewall, a bore extending along the longitudinal axis of the assembly, and a counter-bore extending from the cup member bore along the longitudinal axis and having a diameter greater than that of the cup member bore;
wherein the cup member sidewall surrounds the cup member bore and the cup member counter-bore;
the cup member bore has a diameter approximately equal to a diameter of the bore of the mounting member, and is approximately concentric with, and located adjacent to the mounting member bore to form an extension thereof; and
the first and second contact clips are contained in the cup member counter-bore.

12. The contact assembly of claim 11, wherein:
the mounting member further comprises another shoulder being axially offset from the shoulder that extends about the first and second portions of the perimeter of the bore, the other shoulder extending around the second portion of the perimeter of the bore and being located alongside the second mounting sidewall; and an outer diameter of the cup member sidewall is approximately equal to an outer diameter of the other shoulder of the mounting member.

13. The contact assembly of claim 11, wherein the cup member is formed from a conductive material.

14. The contact assembly of claim 1, wherein the mounting member is formed from a conductive material.

15. The contact assembly of claim 1, wherein the first and second legs of the first and second contact clips make electrical contact with a single connector element of the medical electrical lead connector fully inserted within the bore.

16. A connector assembly for a connector module of a medical device, the connector assembly comprising a first contact assembly and a second contact assembly spaced axially apart from the first contact assembly along a longitudinal bore of the connector assembly, at least one of the first and second contact assemblies comprising:
a mounting member including a bore extending along a longitudinal axis of the contact assembly, a first mounting sidewall extending about a first portion of a perimeter of the mounting member bore, a second mounting sidewall being axially offset from the first mounting sidewall and extending about a second portion of the perimeter of the mounting member bore, the second portion being offset about the perimeter from the first portion by approximately ninety degrees, and a shoulder extending about the first and second portions of the perimeter of the mounting member bore and being axially located between the first and second mounting sidewalls;
a first contact clip mounted on the first mounting sidewall, the first contact clip including a first terminal end and a first leg extending into the mounting member bore and being terminated at the first terminal end on an opposite side of the mounting member bore from the first mounting sidewall, and a second terminal end and a second leg extending into the mounting member bore on an opposite side of the mounting member bore from the first leg, and being terminated at the second terminal end on the opposite side of the mounting member bore from the first mounting sidewall; and
a second contact clip mounted on the second mounting sidewall, the second contact clip including a first terminal end and a first leg extending into the mounting member bore and being terminated at the first terminal end of the second clip on an opposite side of the mounting member bore from the second mounting sidewall, and a second terminal end and a second leg extending into the mounting member bore on an opposite side of the mounting member bore from the first leg of the second contact clip, and being terminated at the second terminal end of the second clip on the opposite side of the mounting member bore from the second mounting sidewall;
wherein the mounting member bore receives axial insertion of a medical electrical lead connector therein.

17. The connector assembly of claim 16, wherein the mounting member of the contact assembly further includes a first opposing sidewall, opposite the first mounting sidewall, being approximately axially aligned with the first mounting sidewall, the first opposing sidewall extending about a third portion of the perimeter of the mounting member bore, the third portion being offset from the first portion by approximately 180 degrees, and a second opposing sidewall, opposite the second mounting sidewall, being approximately axially aligned with the second mounting sidewall, the second opposing sidewall extending about a fourth portion of the perimeter of the mounting member bore, the fourth portion being offset from the second portion by approximately 180 degrees.

18. The connector assembly of claim 17, wherein the first mounting sidewall of the contact assembly and the first opposing sidewall of the contact assembly are symmetric.

19. The connector assembly of claim 17, wherein the first opposing sidewall of the contact assembly interfaces with the first and second legs of the first contact clip in proximity the first and second terminal ends, respectively, of the first clip in order to pre-load the first clip.

20. The connector assembly of claim 16, wherein the shoulder of the contact assembly mounting member extends about an entirety of the perimeter of the mounting member bore.

21. The connector assembly of claim 16, wherein the first and second legs of the first contact clip of the contact assembly bend into and out from the mounting member bore such that the first and second terminal ends of the first clip are located outside the mounting member bore.

22. The connector assembly of claim 16, wherein the first contact clip of the contact assembly is formed from a wire having a round cross-section.

23. The connector assembly of claim 16, wherein the mounting member of the contact assembly further comprises another shoulder being axially offset from the shoulder that extends about the first and second portions of the perimeter of the mounting member bore, the other shoulder extending around the second portion of the perimeter of the mounting member bore and being located alongside the second mounting sidewall.

24. The connector assembly of claim 23, wherein the other shoulder of the contact assembly mounting member extends about an entirety of the perimeter of the mounting member bore.

25. The connector assembly of claim 24, wherein:
the contact assembly mounting member further includes a counter-bore extending from the mounting member bore, along the longitudinal axis, the counter-bore having a diameter larger than that of the mounting member bore; and
the other shoulder of the contact assembly mounting member extends axially away from the second mounting sidewall to surround the counter-bore.

26. The connector assembly of claim 16, wherein the contact assembly further comprises:
a cup member, the cup member including a sidewall, a bore extending along the longitudinal axis of the contact assembly, and a counter-bore extending from the cup member bore along the longitudinal axis and having a diameter greater than that of the cup member bore;
wherein the cup member sidewall surrounds the cup member bore and the cup member counter-bore;
the cup member bore has a diameter approximately equal to a diameter of the bore of the mounting member, and is approximately concentric with, and located adjacent to the mounting member bore to form an extension thereof; and
the first and second contact clips of the contact assembly are contained in the cup member counter-bore.

27. The connector assembly of claim 26, wherein:
the mounting member of the contact assembly further comprises another shoulder being axially offset from the shoulder that extends about the first and second portions of the perimeter of the mounting member bore, the other shoulder extending around the second portion of the perimeter of the mounting member bore and being located alongside the second mounting sidewall; and
an outer diameter of the sidewall of the contact assembly cup member is approximately equal to an outer diameter of the other shoulder of the contact assembly mounting member.

28. The connector assembly of claim 26, wherein the contact assembly cup member is formed from a conductive material.

29. The connector assembly of claim 16, wherein the contact assembly mounting member is formed from a conductive material.

30. The connector assembly of claim 16, wherein the first and second legs of the first and second contact clips make electrical contact with a single connector element of the medical electrical lead connector fully inserted within the mounting member bore.

31. A contact assembly for a connector module of a medical device, the contact assembly comprising:
a sidewall and a bore extending along a longitudinal axis of the contact assembly, the sidewall surrounding the bore and the bore receiving axial insertion of a medical electrical lead connector; and
a first generally u-shaped contact clip and a second generally u-shaped contact clip, each of the first and second contact clips including a pair of opposing curved legs, a pair of terminal ends, and a joining portion extending between each curved leg of the pair opposing curved legs;
wherein the joining portion of each of the first and second clips is attached to the sidewall such that the pair of opposing curved legs of each of the first and second clips bend into and out from the bore, and the pair of terminal ends of each of the first and second clips are located outside the bore;
each curved leg of the pair of opposing curved legs of each of the first and second contact clips includes an inward bending portion and an outward bending portion;
the inward bending portions of each pair of opposing curved legs extend from the corresponding joining portion and bend inward, toward one another; and
each outward bending portion of each pair of opposing curved legs bends outward from the corresponding inward bending portion and extends therefrom to a corresponding terminal end of the pair of terminal ends, such that each terminal end is located along a curvature defining the outward bending of the outward bending portion of the corresponding curved leg.

32. The contact assembly of claim 31, wherein the joining portion of the first contact clip is offset about a perimeter of the bore from the joining portion of the second contact clip by approximately 90 degrees.

33. The contact assembly of claim 31, wherein the joining portion of the first contact clip is axially offset from the joining portion of the second contact clip.

34. The contact assembly of claim 31, wherein the first contact clip is formed from a wire having a round cross-section.

35. The contact assembly of claim 31, wherein the sidewall includes a first portion disposed between the outward bending portions of the pair of opposing curved legs of the first contact clip, in proximity to the terminal ends thereof, in order to pre-load the first clip.

36. The contact assembly of claim 31, wherein the sidewall includes a shoulder located between the first and second contact clips.

37. The contact assembly of claim 31, wherein the sidewall is formed from a conductive material.

38. The contact assembly of claim 31, wherein the pair of opposing curved legs of each of the first and second contact clips make electrical contact with a single connector element of the medical electrical lead connector fully inserted within the bore.

39. A connector assembly for a connector module of a medical device, the connector assembly comprising a first contact assembly and a second contact assembly spaced axially apart from the first contact assembly along a longitudinal bore of the connector assembly, at least one of the first and second contact assemblies comprising:
- a sidewall and a bore extending along a longitudinal axis of the contact assembly, the sidewall surrounding the contact assembly bore and the contact assembly bore receiving axial insertion of a medical electrical lead connector; and
- a first generally u-shaped contact clip and a second generally u-shaped contact clip, each of the first and second contact clips including a pair of opposing curved legs, a pair of terminal ends, and a joining portion extending between each curved leg of the pair opposing curved legs;
- wherein the joining portion of each of the first and second clips is attached to the contact assembly sidewall such that the pair of opposing curved legs of each of the first and second clips bend into and out from the contact assembly bore, and the pair of terminal ends of each of the first and second clips are located outside the contact assembly bores;
- each curved leg of the pair of opposing curved legs of each of the first and second contact clips includes an inward bending portion and an outward bending portion;
- the inward bending portions of each pair of opposing curved legs extend from the corresponding joining portion and bend inward, toward one another; and
- each outward bending portion of each pair of opposing curved legs bends outward from the corresponding inward bending portion and extends therefrom to a corresponding terminal end of the pair of terminal ends, such that each terminal end is located along a curvature defining the outward bending of the outward bending portion of the corresponding curved leg.

40. The connector assembly of claim 39, wherein the joining portion of the first contact clip of the contact assembly is offset about a perimeter of the contact assembly bore from the joining portion of the second contact clip of the contact assembly by approximately 90 degrees.

41. The connector assembly of claim 39, wherein the joining portion of the first contact clip of the contact assembly is axially offset from the joining portion of the second contact clip of the contact assembly.

42. The connector assembly of claim 39, wherein the first contact clip of the contact assembly is formed from a wire having a round cross-section.

43. The connector assembly of claim 39, wherein the contact assembly sidewall includes a first portion disposed between the outward bending portions of the pair of opposing curved legs of the first contact clip of the contact assembly, in proximity to the terminal ends thereof, in order to pre-load the first clip.

44. The connector assembly of claim 39, wherein the contact assembly sidewall includes a shoulder located between the first and second contact clips of the contact assembly.

45. The connector assembly of claim 39, wherein the contact assembly sidewall is formed from a conductive material.

46. The connector assembly of claim 39, wherein the pair of opposing curved legs of each of the first and second contact clips make electrical contact with a single connector element of the lead connector fully inserted within the contact assembly bore.

* * * * *

UNITED STATES PATENT AND TRADEMARK OFFICE
CERTIFICATE OF CORRECTION

PATENT NO. : 7,510,447 B2
APPLICATION NO. : 11/697386
DATED : March 31, 2009
INVENTOR(S) : Michael H. Z. Drew

Page 1 of 1

It is certified that error appears in the above-identified patent and that said Letters Patent is hereby corrected as shown below:

Column 11
Line 31, claim 39 "assembly bores;" should read -- assembly bore; --.

Signed and Sealed this

Eighteenth Day of August, 2009

David J. Kappos
*Director of the United States Patent and Trademark Office*